(12) United States Patent
Shkrob et al.

(10) Patent No.: US 8,722,415 B1
(45) Date of Patent: May 13, 2014

(54) METHOD OF DETECTING LUMINESCENT TARGET IONS WITH MODIFIED MAGNETIC MICROSPHERES

(75) Inventors: Ilya A. Shkrob, Chicago, IL (US); Michael D. Kaminski, Lockport, IL (US)

(73) Assignee: U.S. Department of Energy, Washington, DC (US)

( * ) Notice: Subject to any disclaimer, the term of this patent is extended or adjusted under 35 U.S.C. 154(b) by 87 days.

(21) Appl. No.: 13/038,673

(22) Filed: Mar. 2, 2011

Related U.S. Application Data

(60) Provisional application No. 61/390,629, filed on Oct. 7, 2010.

(51) Int. Cl.
*G01N 33/20* (2006.01)
(52) U.S. Cl.
USPC .................................. 436/82; 436/73; 436/81
(58) Field of Classification Search
USPC ................................................ 436/82, 81, 73
See application file for complete search history.

(56) References Cited

U.S. PATENT DOCUMENTS

| | | | | |
|---|---|---|---|---|
| 5,459,040 | A | * | 10/1995 | Hammock et al. ............. 435/7.1 |
| 2002/0164271 | A1 | * | 11/2002 | Ho ............................ 422/82.08 |

OTHER PUBLICATIONS

Magnetic Extraction, Detectiong, and Isotope Analysis of Metal Ions Using Surface Modified Microspheres for Lab on a Chip Applications Ilya A. Shkrob, Michael D. Kaminski, Kamyar Rahimian, and Mark S. Derzon Separation Science and Technology. 45: 186-197, 2010.*

Sequestration, Fluorometric Detection, and Mass Spectroscopy Analysis of Lanthanide Ions using Surface Modified Magnetic Microspheres for Microfluidic Manipulation Ilya Shkrob, Michael Kaminski, Carol Mertz, Paul Rickert, Mark Derzon, and Kamyar Rahimian J. Am. Chem. Soc. 2009, 131, pp. 15705-15710.*

* cited by examiner

*Primary Examiner* — Krishnan S Menon
*Assistant Examiner* — Dwan A Gerido
(74) *Attorney, Agent, or Firm* — John D. Cravero; Brian J. Lally; John T. Lucas

(57) ABSTRACT

This invention provides methods of using modified magnetic microspheres to extract target ions from a sample in order to detect their presence in a microfluidic environment. In one or more embodiments, the microspheres are modified with molecules on the surface that allow the target ions in the sample to form complexes with specific ligand molecules on the microsphere surface. In one or more embodiments, the microspheres are modified with molecules that sequester the target ions from the sample, but specific ligand molecules in solution subsequently re-extract the target ions from the microspheres into the solution, where the complexes form independent of the microsphere surface. Once the complexes form, they are exposed to an excitation wavelength light source suitable for exciting the target ion to emit a luminescent signal pattern. Detection of the luminescent signal pattern allows for determination of the presence of the target ions in the sample.

16 Claims, 7 Drawing Sheets

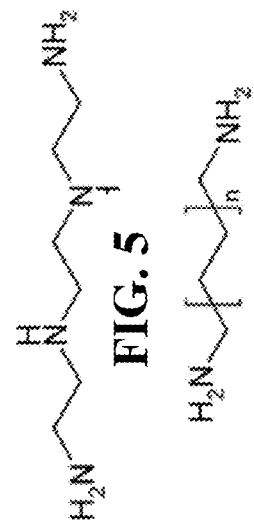
FIG. 5
FIG. 6
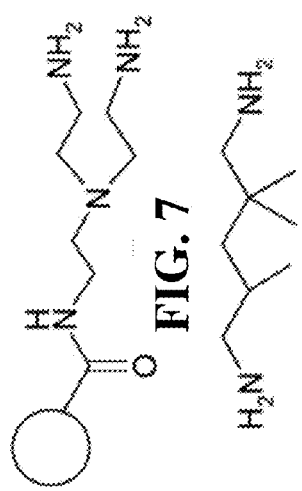
FIG. 7
FIG. 8
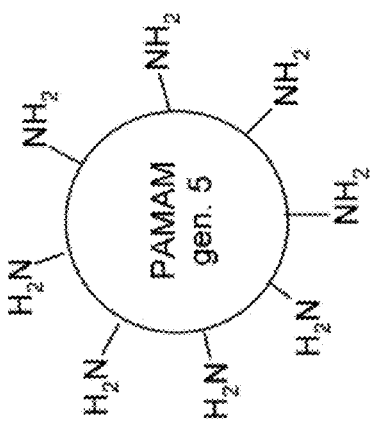
FIG. 12
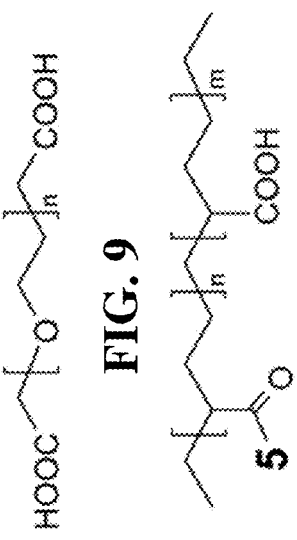
FIG. 9
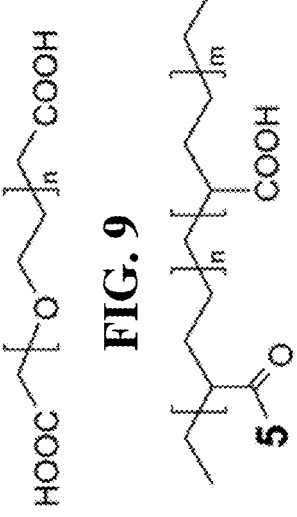
FIG. 10
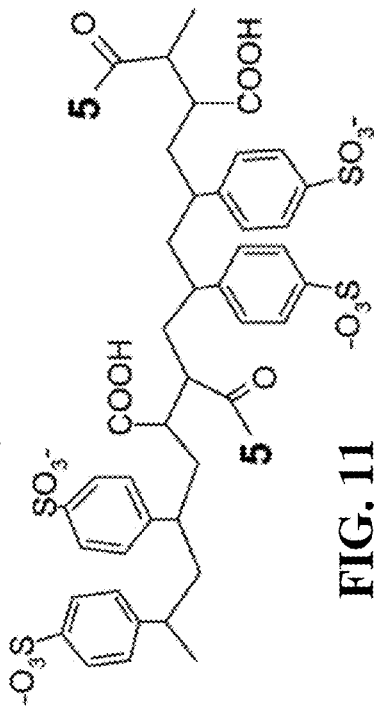
FIG. 11

METHOD OF DETECTING LUMINESCENT TARGET IONS WITH MODIFIED MAGNETIC MICROSPHERES

CROSS-REFERENCE TO RELATED APPLICATIONS

This patent claims priority to and the benefit of U.S. Provisional Application No. 61/390,629 filed on Oct. 7, 2010, the entirety of which is hereby incorporated by reference.

GOVERNMENT INTERESTS

The United States Government has rights in this invention pursuant to Contract No. DE-AC02-06CH11357, between the U.S. Department of Energy (DOE) and UChicago Argonne LLC, representing Argonne National Laboratory.

FIELD OF THE INVENTION

One or more methods consistent with the present disclosure relate to the sequestration and detection of metal target ions in a sample and, more specifically, to a method of detecting luminescent target ions in a sample using modified magnetic microspheres. One or more methods may be capable of implementation in a portable, microfluidic device.

BACKGROUND

Detecting trace amounts of metal ions, such as fission products and radionuclides that result from nuclear reactions, is important for nuclear forensics. In addition, certain rare earth metal ions pose environmental and health risks, so accurate detection of such ions would be advantageous for environmental chemistry, biological chemistry, and medical diagnostics.

Two current approaches for sequestration of metal ions from samples are liquid-liquid extraction and ion-exchange chromatography. To maximize practicality, it is desirable to adapt these techniques to microfluidic environments, which would speed up the sequestration process and allow for application to portable nuclear detection devices. However, miniaturizing these techniques is challenging because small sample volumes require detection techniques to have low detection limits, fast response times, and high selectivity. Thus, there exists a need for increasingly sophisticated methods for the detection of trace amounts of certain metal ions in environmental samples that could be adaptable to portable devices.

The present invention addresses the problem of efficiently isolating and detecting trace concentrations of f-elements in environmental samples through the use of modified magnetic microspheres. The microspheres provide a platform for efficient and selective target ion extraction. Additionally, the microspheres' magnetic property allows for manipulation of their movement in microfluidic environments. The ability to control the movement of the microspheres is critical considering that molecular interactions in microfluidic environments are dominated by factors such as surface tension, energy dissipation, and fluidic resistance.

SUMMARY

One or more embodiments of the present invention relate to methods of extracting and detecting target ions in environmental samples. The embodiments are particularly useful for detecting trace elements including but not limited to lanthanide and actinide ions ("f-block elements"), radionuclides, and radiological agents that are of interest to nuclear forensics, geochemistry, immunoassay analyses, and analytical chemistry. The embodiments are additionally useful for their ability to be implemented in a portable, field deployable analytical device, such as a microfluidic device.

One or more embodiments of the present invention utilize modified magnetic microspheres for sequestration of target ions from a sample onto the surface of the microspheres, where the ions can be manipulated. The magnetic microspheres are particularly advantageous for implementation in a portable device because they provide new degrees of freedom for handling the sample during multistage separations and pre-concentration stages.

One or more embodiments of the present invention are directed to sensitive and specific luminescence assays for detection of trace amounts of f-elements in liquid solution by isolating f-element ions from a solution containing f-element ions onto the surface of magnetic microspheres. The modified magnetic microspheres can be manipulated inside a microfluidic device. Similar approaches may use particles smaller or larger than the microspheres described herein.

In one or more embodiments, the general sequestration and detection approach is to form a ligand/luminescent-metal/ligand-complex wherein the target luminescent metal ion is sandwiched between two or more ligands. The ligands that bind to the metal ion and form the luminescent complex may be referred to as a co-ligand and an antenna ligand.

In one or more embodiments, detection of the target ion is accomplished through time-resolved laser fluorescence spectroscopy (TRLF), wherein the antenna ligand absorbs a photon of excitation light and channels the energy to the bound metal ion. The excited target ion subsequently re-emits light that is detected by a fluorimeter in a time-resolved fashion which provides ion selectivity.

One or more embodiments utilize a type of magnetic microsphere that features a non-reactive barrier, such as a coating of gold film, carbon, oxide or a polymer outer layer or overcoat. The non-reactive barrier, e.g., polymer outer layer, is particularly advantageous as it isolates the metal core of the microsphere from the surface and prevents metal ions in the core from quenching the luminescent complexes attached to the microsphere surface. The non-reactive barrier may have functional groups such as thiols, carboxyl or amine groups.

One or more embodiments of the invention feature an amphiphilic compound, such as a detergent, in the microsphere solutions that suspends the microspheres to protect the subsequently formed luminescent complexes from luminescence-quenching water molecules and ions in the aqueous environment. Additionally, in one or more embodiments, the amphiphilic compound has characteristics that prevent both the aggregation of microspheres and the formation of micelles in the bulk solution which would extract luminescent complexes and provide unwanted background luminescence.

In another embodiment, the present invention relates to a method of extracting and detecting target ions in a sample using magnetic microspheres that are modified by the attachment of a first ligand to the surface of the microspheres. A solution comprising the magnetic microspheres modified with the first ligand is mixed with a second solution comprising a target ion and a third solution comprising a second ligand to form a detection solution. In the detection solution, the first ligand attached to the microsphere binds to the target ion, which in turn binds to the second ligand resulting in the formation of one or more luminescent complexes on the surface of the magnetic microsphere. Next, the detection solution is excited and the resulting luminescent response of the complexes is detected, preferably using a time-resolved fluorescence detection method.

In one or more embodiments of the present invention, a first ligand is attached to the magnetic microsphere by a covalent bond between the ligand and a functional group on the surface of the microsphere. In one or more embodiments, the first ligand covalently attached to the microsphere is the co-ligand of the subsequently formed luminescent complex. In these embodiments, the antenna ligand is the second ligand contained in the third solution. Once all three solutions are mixed together, one or more luminescent complexes form on the surface of the magnetic microspheres in the detection solution.

In other embodiments, the first ligand covalently attached to the microsphere is the antenna ligand, and the co-ligand is the second ligand introduced by the third solution.

In one or more embodiments, the first ligand is attached to the surface of the magnetic microsphere by weak intermolecular forces instead of covalent bonds. In one or more embodiments, the first ligand is the co-ligand, and the antenna ligand is the second ligand. Although the forces connecting the co-ligand to the microsphere are weak, the co-ligand is stabilized at the surface of the microsphere by maintaining high ionic strength in the detection solution.

One or more additional embodiments of the present invention relate to a method of extracting and detecting target ions in a sample using magnetic microspheres that are modified by the attachment of hydrophobic chains to the surface of the microspheres. The microspheres, although covered by hydrophobic chains, are suspendable in aqueous solutions by the addition of a detergent in some embodiments, and by covalent attachment to hydrophilic compounds in other embodiments. In these embodiments, a solution comprising these modified magnetic microspheres is mixed with a second solution comprising the target ion and a third solution comprising both an antenna ligand and a co-ligand to form a detection solution. In the detection solution, the luminescent complexes that form between co-ligands, target ions, and antenna ligands get extracted into the hydrophobic layer on the surface of the microspheres. A solution comprising the complexes is subsequently exposed to excitation energy and the target ion is detected using one or more detection methods described herein.

One or more additional embodiments of the present invention relate to a method of extracting and detecting target ions in a sample using magnetic microspheres that are modified with a functional group. In these embodiments, the modified microspheres are first mixed with a solution comprising the target ion, wherein the functional group on the microspheres extracts the target ion, forming a non-luminescent complex on the microspheres. The microspheres are magnetically separated and then mixed with a second solution comprising a co-ligand and an antenna ligand to form a detection solution. In the detection solution, the free-floating co-ligands and antenna ligands re-extract the target ions from the microspheres and form luminescent complexes in the detection solution. Unlike other embodiments of this present invention, the resulting luminescent complexes are not attached to the magnetic microspheres.

In one or more embodiments of the present invention, luminescent assay methods like the ones mentioned above are used to detect the presence of non-luminescent target ions in a sample. In these embodiments, magnetic microspheres pre-loaded with a known concentration of luminescent ions are contacted with non-luminescent ions in a solution, wherein the non-luminescent ions exchange places with the luminescent ions. The concentration of displaced luminescent ions in the solution can be detected using one of the luminescent assay methods. Finally, the concentration of non-luminescent ions can be estimated by subtracting the detected concentration of displaced luminescent ions from the known original concentration of luminescent ions pre-loaded on the magnetic microspheres.

BRIEF DESCRIPTION OF THE DRAWINGS

These and other features, aspects, and advantages of the multiple embodiments of the present invention will become better understood with reference to the following description, appended claims, and accompanied drawings where:

FIGS. 5-12 are schematic representations of exemplary spacers that bind a co-ligand to a microsphere surface in one or more embodiments of the present invention.

DETAILED DESCRIPTION

Figure 4:
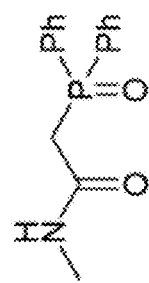
FIGS. 1-4 are schematic representations of exemplary co-ligands that are compatible with one or more embodiments of the present invention.

Generally, the present invention is directed to various methods of using magnetic microspheres to aid in the formation of luminescent complexes for the detection of target ions. The magnetic microspheres aid the detection by extracting the target ions from a sample and, in some methods, providing a surface on which the luminescent complex may form, which immobilizes the target ion and allows for manipulation in the fluidic environment. The ability to manipulate the magnetic microspheres is important for implementing these assay methods in portable detection devices.

In some of the embodiments of the present invention the luminescent complex forms on the surface of the magnetic microsphere, which immobilizes the target ion. This is accomplished by modifying the microspheres in different ways. In some embodiments, a co-ligand molecule which forms part of the luminescent complex is attached to the microspheres. In some of these embodiments, the co-ligand attaches to the microsphere surface through covalent bonding, while in other embodiments weak molecular forces connect the co-ligand to the surface of the microsphere due to high salinity conditions in the solution. In other embodiments, an antenna molecule that forms part of the luminescent complex is attached to the microspheres through covalent bonding. In yet another embodiment, the magnetic microspheres are modified by the attachment of hydrophobic chains to the microsphere surface which extracts the luminescent complexes into a hydrophobic layer that forms between the microsphere and a hydrophilic outer layer.

In one or more embodiments of the present invention, a modified magnetic microsphere is used to sequester a target ion from a sample solution. Subsequently, a co-ligand and an antenna ligand are used to re-extract the target ion from the microsphere to form a luminescent complex in the solution independent of the magnetic microsphere. The solution comprising the complexes is subsequently exposed to excitation energy and the target ion is detected using one or more detection methods.

DEFINITIONS

Before describing the present invention in detail, it is to be understood that this invention is not limited to specific compositions or process steps, as such may vary. It must be noted that, as used in this specification and the appended claims, the singular form "a", "an", and "the" include plural referents unless the context clearly dictates otherwise. Thus, for example, reference to "a target ion" may include a plurality of ions.

Unless defined otherwise, all technical and scientific terms used herein have the same meaning as commonly understood by one of ordinary skill in the art to which this invention in related. The following terms are defined for purposes of the invention as described herein.

The term "target ion" refers to charged molecules of a specific element, the detection of which is one purpose of the invention. For example, in one or more preferred embodiments, the target ion is a lanthanide or an actinide element. In a more preferred embodiment, the target ion is Eu, Am, Tb, U and combinations thereof.

The term "luminescent ion" refers to a charged molecule that emits light after it has absorbed light of a defined wavelength. These ions include but are not limited to lanthanide ions which comprise elements with atomic numbers 58-71 in the periodic table. In one preferred embodiment, europium ($Eu^{3+}$) is the luminescent ion, but other luminescent ions may be used. A luminescent ion absorbs energy and emits it at a specific wavelength, which can be detected to show the presence of the ion.

In one or more embodiments of the present invention, the luminescent ion is also the target ion. Thus, the terms "luminescent target ion," "target ion," and "luminescent ion" may be used interchangeably in certain instances.

The term "sample" as used herein refers to any material or solution that may contain target ions, as described above.

The term "magnetic microspheres" refers to substantially spherical particles with diameters on the nanometer to the millimeter scale that have a magnetic core which make the particles subject to magnetic manipulation. In one or more preferred embodiments, the microspheres include a non-reactive barrier or coating, such as a polymer overcoat. In one or more preferred embodiments, the microspheres have specific functional groups on their surface.

The term "attachment" or "attach" as used herein refers to any chemical bond between two molecules or compounds, including intramolecular ("strong") bonds, including but not limited to covalent, ionic and metallic bonds, and intermolecular ("weak") bonds, including but not limited to hydrogen bonds and other noncovalent bonds, such as van der Waals forces, London dispersion forces, and mechanical bonds. It may also include intervening molecules between the two molecules said to be attached to each other. For example, a modified magnetic microsphere may be attached to a co-ligand through an intervening spacer molecule that physically connects the microsphere to the co-ligand.

The term "ligand" as used herein refers to one or more molecules or ions that bind to a central metal ion (e.g., target ion) to form a complex. In one or more embodiments, "ligand" is divided into two classes, "antenna ligand" and "co-ligand," based on the function of the molecule as described herein.

The term "antenna ligand" refers to any compound capable of binding to a luminescent ion along with a co-ligand to form a luminescent complex. Upon excitation by light or other electromagnetic radiation, the antenna ligand absorbs the energy from the excitation and transfers the energy to the luminescent ion, which then re-emits the energy as a different wavelength light.

The term "co-ligand" as used herein refers to a compound that binds to a luminescent ion along with an antenna ligand to form a luminescent complex. The co-ligand's functions include binding to and sequestering target ions from the target ion solution, stabilizing the ions, and shielding them from external molecules. Generally, preferable co-ligands are strongly chelating, hydrophobic ligands without light quenching chemical groups, e.g., hydroxyl groups.

The term "complex" as used herein refers to the association of two or more molecules, one of which as used herein is a target ion.

The term "luminescent complex," "co-ligand/target ion/antenna ligand complex," or "ligand complex" can be used interchangeably to refer to the association between the luminescent target ion, co-ligand, and antenna ligand which is necessary to support the absorption and subsequent emission of light energy by the luminescent ion. In one or more preferred embodiments, the co-ligand and antenna ligand sandwich the luminescent ion to form the luminescent complex.

The term "luminescent response" refers to the light that is emitted by the luminescent ion after absorbing the energy captured by the antenna ligand in the luminescent complex.

The term time-resolved laser fluorescence spectroscopy (TRLF) refers to one of multiple methods for detecting the luminescent response. This method consists of illuminating the detection solution and detecting the timing and strength of the light emitted by the luminescent complex.

The term "non-luminescent complex" as used herein refers to any association between a target ion and a molecule that would not emit a luminescent response upon excitation. It refers to all complexes formed with non-luminescent target ions, and also includes complexes between luminescent target ions and co-ligands that lack antenna ligands.

The term "detection solution" as used herein refers to the solution in which luminescent complexes are formed, whether or not on the microsphere surface, and in which the excitation light for the detection of luminescence is applied.

The term "aqueous solution" as used herein refers to a solution that is predominantly water and retains the solution characteristics of water. Where the aqueous solution contains solvents in addition to water, water is typically the predominant solvent.

The term "functional group" refers to a specific grouping of elements that is characteristic of a class of compounds, and determines some properties and reactions of that class.

The term "carboxyl" or "carboxylated" refers to a compound containing one or more functional groups having the formula —COOH.

The term "amino," "amine," or "aminated" refers to a compound containing one or more functional groups having the formula —NH$_2$.

The term "spacer molecule" as used herein refers to a molecule that serves to link a microsphere to a ligand.

The term "diamine" as used herein refers to any compound containing two amino functional groups with a hydrocarbon chain between them.

The term "contact," "contacting," and "mixing" can be used interchangeably and refers to mixing or combining one or more substances, including but not limited to liquids and solid particles. For example, in one step of one or more embodiments of the present invention, "contacting" refers to combining microspheres or a solution containing microspheres with a second solution and letting the components within the mixture interact.

The term "critical micelle concentration" refers to the surfactant concentration in a solution at which micelles start to form.

I. Ligand Attachment Assay

In one or more embodiments of the present invention, magnetic microspheres are modified through attachment of a first ligand molecule which is capable of binding to a target ion. Various embodiments of modified magnetic microsphere complexes compatible with one or more embodiments of the present invention are depicted in FIGS. 22A-F, where "MM" is a magnetic microsphere, "L" is a co-ligand, "A" is an antenna ligand and M$^{n+}$ is a metal target ion. After the first ligand is attached to the microsphere, a solution of these modified magnetic microspheres is mixed with a solution comprising a target ion and a solution comprising a second ligand.

Since the luminescent complex forms on the surface of the microsphere in this embodiment, the microspheres must not interfere with luminescence. Most commercially-available magnetic microspheres contain dispersed magnetic nanoparticles near the microsphere surface, which quench the luminescence. However, a preferred type of microsphere contains a polymer overcoat that effectively isolates the metallic molecules in the core from the luminescent complexes on the surface. In a preferred embodiment, the magnetic microspheres have a protective overcoat of polystyrene. In yet another embodiment, the microsphere may have a non-reactive barrier, such as a coating of gold film, carbon or oxide, with functional groups bonded to the non-reactive barrier. The microspheres may have sulfonate functional groups at their surface, and may also or separately contain thiol, carboxyl- or amino-functional groups as well.

In one embodiment of the present invention, the first ligand is attached to the magnetic microsphere through a covalent bond and performs the role of a co-ligand in the eventual luminescent complex. This assay is referred as the "covalent co-ligand assay." The co-ligands attached to the microspheres are either amino- or carboxyl-terminated, which allows them to bind covalently to functional groups on the microsphere surfaces. Additionally, the co-ligands have to be able to bind the target ion while providing some shielding effects for the ion as well.

Generally, the co-ligands may include aminocarboxylic acids, organophosphates and phosphines and their amides. The co-ligands in one or more preferred embodiments are phosphine oxides, glycolamides and bidentate imide moieties. Even more preferred co-ligands include triphenylphosphine oxide (TPO), trioctylphosphine oxide (TOPO), tributyl phosphate (TBP), carbomoyl methyl phosphine oxide (CMPO), and other lanthanide/actinide extracting agents. These polydentate co-ligands are sufficiently hydrophobic, strongly bind to the metal ions, and do not have light-quenching groups, such as —OH groups.

Figure 3:
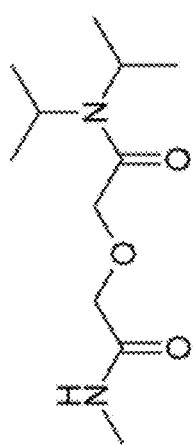
Figure 2:
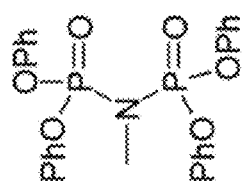
Figure 1:
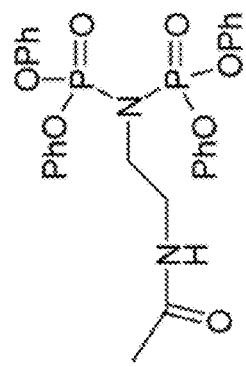

In one or more preferred embodiments, the co-ligand can include, but is not limited to, (diphenylphosphoryl)acetic acid (FIG. 1), N,N'-bis(di-2-propyl)glycolamide (FIG. 2), di(diphenylphosphoric) imide (FIG. 3), di(diphenylphosphoric) (2-aminoethyl) imide (FIG. 4), and combinations thereof. These co-ligands may be synthesized as described in Shkrob et al., *J. Am. Chem. Soc.* 2009, 131, 15705-15710, (Supplementary material, S3-S4), and Shkrob, et al., *Sep. Sci. & Techn.*, 45: 186-97, 2010, which are incorporated by reference herein, or any other method known to one of skill in the art. In additional embodiments, co-ligands not described above may be used as long as they are able to attach to the microsphere surface and form a bond with a target ion when introduced to a solution containing the target ion and magnetic microsphere.

Alternatively, in some embodiments, a spacer molecule can be covalently bonded to both the co-ligand and the magnetic microsphere thereby linking the two molecules. Spacer molecules can include but are not limited to polyamines, polyethylene glycols, polyamidoamide dendrimers, and polymers. Preferred spacer molecules are shown in FIGS. 5-12.

Following formation of the modified microsphere, the magnetic microspheres may be repeatedly washed with a solvent, by suspension in a new portion of the solvent, followed by magnetic separation and removal of the supernate. The preferred organic solvents for washing the magnetic microspheres are methanol, ethanol, dimethylsulfoxide, N,N'-dimethylformamide, and acetonitrile. The last couple of washes are with a non-ionic detergent, and the resulting modified microspheres are suspended in a solution containing detergent to prevent microsphere aggregation in an aqueous environment. One preferred detergent for suspension is the non-ionic detergent N-decanoyl-N-methyl glucamine, MEGA 10, because it has a high critical micelle concentration of about 0.25 wt %. Other detergents having high critical micelle concentrations will also be compatible with one or more embodiments of the present invention. More specifically, any ionic detergent that coats the microspheres, while at the same time, does not allow micelles to form is compatible with the embodiments described herein, i.e., the concentration required to form coats around the microspheres are lower than the critical micelle concentration. In a preferred embodiment, the resulting suspended modified magnetic microsphere solution contains about 2.5 wt % modified microspheres; however, the final concentration of modified microspheres can be adjusted depending on experimental conditions.

In another embodiment, the first ligand which attaches to the magnetic microsphere is a co-ligand, but instead of covalently binding to the magnetic microsphere, weak van der Waals forces between the co-ligands and the surface of the microspheres hold the co-ligands in place. This assay is referred to as the "physisorption" method. In one or more embodiments, the co-ligands are able to form the equivalent of monolayer coverage around the microsphere without inducing microsphere aggregation by maintaining high ionic strength in the solution.

In a preferred embodiment, the co-ligands are phosphine oxides and the ionic strength in the solution is created and maintained through the addition of an ionic compound, such as sodium chloride. The co-ligand is introduced to the magnetic microspheres in a solution containing the ionic compound and a small amount of non-ionic detergent. In the solution, metal cations from the ionic compound interact with polar P=O groups of the co-ligands, and the repulsion between ionic atmospheres provides stability to the modified magnetic micro spheres.

Figure 13:
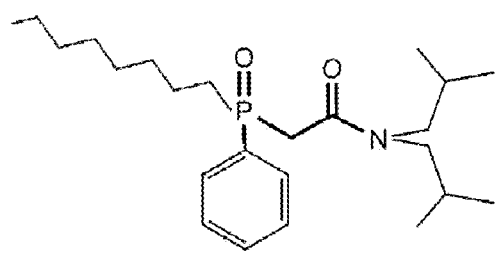
FIGS. 13-16 are schematic representations of additional exemplary co-ligands that are compatible with one or more embodiments of the present invention.
Figure 14:
Figure 15:
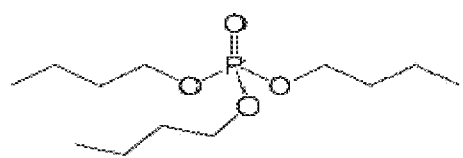
Figure 16:
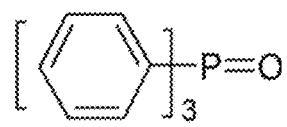

In a preferred embodiment, the phosphine oxide co-ligand is carbamoyl methyl phosphine oxide (CMPO)(FIG. 13), trioctylphosphine oxide (TOPO)(FIG. 14), or a mixture of CMPO or TOPO with tributyl phosphate (TBP) (FIG. 15). In a preferred embodiment, the ionic compound is NaCl, and the concentration of NaCl in the solution is around 10-20 wt %. In a preferred embodiment, the detergent used is 0.01 wt % MEGA 10.

In additional embodiments, co-ligands not described above may be used as long as they are able to attach to the microsphere surface and form a bond with a target ion when introduced to a solution containing the target ion.

Figure 17:
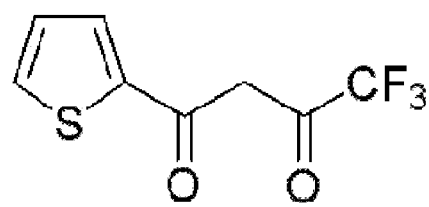
FIG. 17 is a schematic representation of one antenna ligand compatible with one or more embodiments of the present invention.

In yet another embodiment, the first ligand which attaches to the magnetic microsphere is an antenna ligand that is attached through a covalent (for example, peptide) bond with an amine or carboxyl group on the microsphere surface. This assay is referred to as the "covalent antenna" method. In a preferred embodiment, the antenna ligand which binds to the microsphere surface is 2-thenoyltrifluoroacetone (TTA) (FIG. 17). Many of such antenna ligands are beta-diketones substituted with aromatic groups, phenanthroline derivatives, acetylacetone derivatives, and other aromatic polydentate chelating molecules. However, any compound that is capable of absorbing energy of a specific wavelength and transferring that energy to the target ion may be used as an antenna ligand. Prior to attachment, the antenna molecules may be functionalized through covalently binding sulfonyl functional groups, which are capable of binding to amino groups on the magnetic microsphere surface. Alternatively, the functionalized antenna may first be covalently bound to a spacer molecule which is then attached to the microsphere surface, providing a link between the antenna molecule and the microsphere. Examples of spacer molecules include but are not limited to polyamines, polyethylene glycols, polyamidoamide dendrimers, polymers, and combinations thereof.

After modification of the magnetic microspheres through one of the methods described above, a solution of the modified microspheres is mixed with a solution of the target ion and another solution comprising a second ligand. In a preferred embodiment, the target ion is a lanthanide or actinide ion, preferably selected from the group consisting of Eu, Tb, Am, U and combinations thereof, and even more preferably is europium ($Eu^{3+}$). The target ion may be contained in an acidic solution. In preferred embodiments, the target ion solution has a pH less than about 7. More preferably, the solution containing the target ion is about $10^{-4}$ M nitric acid.

In both the covalent co-ligand and physisorption methods described above, the second ligand solution that mixes with the modified microsphere solution and the target ion solution comprises an antenna ligand. In preferred embodiments, the second ligand solution may be an aqueous solution containing TTA.

In the covalent antenna method, the second ligand solution comprises a co-ligand that is used in the formation of the luminescent complex. In preferred embodiments, the co-ligands in this solution are suspended in a detergent. In a preferred embodiment, the co-ligand is CMPO, and the detergent is Triton X-100; however, any non-ionic detergent is acceptable. In a preferred embodiment, the solution comprises 0.5 mM CMPO suspended in 0.1 wt % Triton X-100.

Upon mixing the modified magnetic microsphere, target ion and second ligand solutions, one or more luminescent complexes between the co-ligand, target ion, and antenna ligand are formed on the surface of the magnetic microspheres. The resulting solution is referred to as the "detection solution."

The presence of one or more luminescent complexes in the detection solution is subsequently determined through the illumination of the detection solution with an appropriate wavelength light to excite a luminescent response from the target ion. In a preferred embodiment, the detection solution can be illuminated with 355 nm light.

To determine if any target ions are present, the luminescent response of the detection solution to the stimulus of illumination can be detected using fluorescence spectroscopy. In preferred embodiments, time resolved laser fluorescence ("TRLF") spectroscopy is used to detect the target luminescent ion. TRLF measures the signal strength of the luminescent response over time and allows for specificity because a luminescent ion will re-emit light at a specific time after receiving the stimulus, which is referred to as the luminescent lifetime. In additional embodiments, the target ion may be detected using various mass spectroscopic techniques, including but not limited to electrospray ionization, inductively coupled plasma and laser desorption ionization.

II. Pre-Extraction Assay

In one or more embodiments of the present invention, magnetic microspheres are modified through attachment of a co-ligand, which is capable of extracting target ions from a target ion solution. In these embodiments, the initial steps of modifying the magnetic microspheres are exactly the same as for the embodiments referred to as the covalent co-ligand and physisorption method. That is, the embodiments referred to as the "pre-extraction" method use the same polymer-coated/non-reactive barrier magnetic microspheres, the same co-ligands, and the same steps to attach the co-ligands to the microsphere surface and extract or detect the same target ions as are described in the covalent-co-ligand and physisorption methods.

In one or more embodiments of the pre-extraction method, a solution of modified magnetic microspheres is mixed with a solution comprising a target ion, wherein one or more co-ligands extract the target ions onto the modified microsphere surface forming one or more co-ligand/target ion complexes. In a preferred embodiment, the target ion is europium ($Eu^{3+}$), and it is introduced to the modified magnetic microspheres in an acidic solution. In preferred embodiments, the acidic solution comprising the target ion is around $10^{-4}$ M nitric acid. After mixing, the modified microspheres are magnetically separated from the solution by applying a magnetic field gradient to the solution. This can be accomplished by inserting a magnetic material into solution (e.g., magnetic wire or bar) or against the vessel or microfluidic channel, or creating an electromagnetic field using electric coils. The magnetic field retains the modified microspheres while the solution is removed.

In one or more embodiments, the next step involves contacting the magnetically-separated microspheres that comprise co-ligand/target ion complexes with a solution comprising an antenna ligand to form a detection solution. In the detection solution, the antenna ligands bind to the co-ligand/target ion complexes to form one or more luminescent complexes on the microsphere surface. In a preferred embodiment, the antenna ligand is TTA. The antenna ligand solution in one embodiment comprises the antenna ligand and either a detergent or an ionic compound. For the covalent co-ligand attachment method, the antenna ligand solution may comprise TTA in a non-ionic detergent. For the physisorption method, the antenna ligand solution may comprise TTA in NaCl and a non-ionic detergent. However, various concentrations of antenna ligand, ionic compound and detergent will achieve the result of forming luminescent complexes.

Finally, the detection solution is illuminated with an appropriate wavelength light to excite a luminescent response from the luminescent complexes. In preferred embodiments, the detection solution is illuminated with 355 nm light.

To determine if any target ions are present in the initial target ion solution, the luminescent response of the detection solution to the stimulus of illumination is detected using fluorescence spectroscopy, but any of the methods described herein are compatible. In preferred embodiments, time-resolved laser fluorescence spectroscopy is used to detect the target luminescent ion because this calculation method measures the signal strength of the luminescent response over time, which can provide element specificity.

III. Supermicelle Assay

In one or more additional embodiments of the present invention, magnetic microspheres can be modified through covalent attachment of a hydrophobic chain which forms a vesicle-like double layer at the surface of the microsphere when surrounded by a hydrophilic compound. After the vesicle-like double layer forms around the microsphere, a solution of suspended modified magnetic microspheres is mixed with a solution comprising a target ion and a solution comprising both a co-ligand and an antenna ligand. In the resulting solution, one or more luminescent complexes form between the co-ligand, target ion, and antenna ligand, and the complexes are extracted onto the hydrophobic shell at the microsphere surface.

In a preferred embodiment of the present invention, the magnetic microspheres have a protective overcoat of polystyrene. The microspheres may have sulfonate functional groups at their surface, and some may also be functionalized by either carboxyl- or amino-groups as well.

Figure 18:
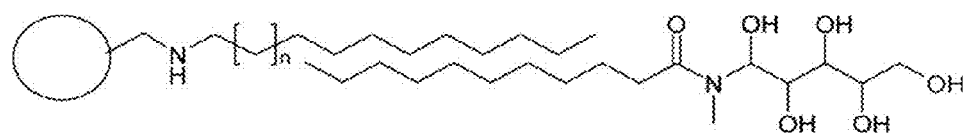
FIG. 18 is a schematic representation of a magnetic microsphere modified through attachment of a hydrophobic alkyl chain suspended in a non-ionic detergent as described in one or more embodiments of the present invention.

In a preferred embodiment, the vesicle-like double layer around the magnetic microsphere is formed by covalent attachment of an alkyl chain molecule to a functional group on the microsphere surface, followed by suspending the modified microsphere in a detergent with a critical micelle concentration greater than about 0.2 wt % to prevent aggregation. In a preferred embodiment, the alkyl chain consists of between 10-22 carbon molecules, and the detergent is non-ionic. In a preferred embodiment, a $C_{10}$-$C_{22}$ chain is covalently bound to an amino group on the microsphere surface, and the modified microsphere is suspended in a non-ionic detergent. A modified microsphere of this embodiment is generally depicted in FIG. 18. More generally, in one or more embodiments, the modified microsphere is formed by mixing an alkyl halide (such as 1-bromododecane) with magnetic microspheres having amino-functional groups in a solvent, such as a methanol/iso-propanol mixture saturated with NaOH, and refluxing the mixture for about 24 hours, although other methods known to one of skill in art can be used.

In another preferred embodiment, the vesicle-like double layer around the microsphere is formed by covalently attaching a molecule with a hydrophobic chain (such as a diamine) to a functional group on the microsphere surface, followed by covalently attaching a hydrophilic molecule (such as a polyethylene glycol oligomer) to the other end of the hydrophobic chain molecule. The resulting compounds attached to the microsphere surface are amphiphilic in nature, since the chains are hydrophobic near the surface but have hydrophilic tails, which prevent the microspheres from aggregating in aqueous solution. Thus, no detergent is necessary in this embodiment.

Figure 19:
FIG. 19 is a schematic representation of a magnetic microsphere modified through attachment of an aliphatic chain bound to a polyether.

In a preferred embodiment, the molecule with a hydrophobic chain is a diamine, and the hydrophilic compound that binds to the diamine is a polyether. In a preferred embodiment, the functional group on the microsphere that binds to one end of the diamine is a carboxyl group, and the polyether compound that binds to the diamine's other end is a carboxylated polyethylene glycol (PEG) oligomer (FIG. 19).

After the vesicle-like double layer is formed on the magnetic microspheres, the suspended microsphere solution is mixed with a solution comprising a target ion and a second solution comprising both a co-ligand and an antenna ligand. In one or more embodiments, the target ion is europium ($Eu^{3+}$), and is introduced to the modified magnetic microspheres in a weakly acidic solution. In one preferred embodiment, the acidic solution containing the target ion is around $10^{-4}$ M nitric acid. In preferred embodiments the co-ligand and the antenna ligand of the second solution are TBP and TTA, respectively. In preferred embodiments, the second solution is an aqueous solution comprising between about 0.75 mM TTA and 0.25 mM TBP.

Upon mixing these three solutions, one or more luminescent complexes between the co-ligand, target ion, and antenna ligand form in the resulting detection solution, and the vesicular surface extracts one or more such complexes into the hydrophobic layer of the magnetic microsphere. The free complexes remaining in the solution do not luminesce because water molecules act as luminescence quenchers.

Finally, the detection solution is illuminated with an appropriate wavelength light to excite a luminescent response. In preferred embodiments, the detection solution is illuminated with 355 nm light.

To determine if any target ions are present in the initial target ion solution, the luminescent response of the detection solution to the stimulus of illumination is detected using fluorescence spectroscopy. In preferred embodiments, time-resolved laser fluorescence spectroscopy is used to detect the target luminescent ion because this calculation method measures the signal strength of the luminescent response over time, which provides element specificity.

IV. Solution-Based Assay

In one or more additional embodiments of the present invention, magnetic microspheres are modified with a functional group that, when mixed with target ions in a solution, binds to and sequesters target ions onto the surface of the modified microsphere.

The magnetic microspheres used in this assay method do not have to be insulated by a non-reactive barrier or polystyrene overcoat because the luminescent complexes do not form on the microsphere surface in this method, but rather in a detection solution independent of the microspheres. Thus, the presence of luminescent-quenching ions within the microsphere cores will not quench free-floating luminescent complexes in solution.

In one or more preferred embodiments of the present invention, the microsphere is functionalized by an aminocarboxylic acid which sequesters the target ions from the target ion solution. In a preferred embodiment, the microsphere may be comprised of cellulose (e.g., SEPHAROSE®) and conjugated with ethylenediaminetetraacetic acid (EDTA) at the surface. In another preferred embodiment, the microsphere may be comprised of silica and conjugated with iminoacetic acid (IDA). However, it is believed that any microsphere modified with an aminocarboxylic acid will be capable of extracting a target ion and, thus, would be compatible with the currently described embodiment. Moreover, it is envisioned that any ligand that has a sufficiently strong affinity for a target ion can be attached to the microsphere surface; such ligands include but are not limited to phosphine oxides, amines, phosphinic acids, thiols and combinations thereof.

For the initial sequestration, the modified magnetic microspheres can be suspended in solution by a detergent, and that solution is mixed with a solution comprising a target ion. In one or more preferred embodiments, the detergent is non-ionic, but cationic and anionic detergents yield similar results in preventing the microspheres from aggregating in solution. In a preferred embodiment, the detergent is a polyethylene glycol-terminated non-ionic detergent, such as Triton X-100. In preferred embodiments, the target ion is europium ($Eu^{3+}$), and is introduced to the modified magnetic microspheres in an acidic solution with a pH less than about 7. However, the method is applicable to other target ions, including but not limited to lanthanide and actinide elements. In preferred embodiments, the acidic solution comprising the target ion is around $10^{-4}$ M nitric acid. Upon mixing, the modified magnetic microspheres sequester target ions from the solution onto the microsphere surfaces. After mixing, the modified microspheres are magnetically separated from the solution by applying a magnetic field gradient to the solution. This can be accomplished by inserting a magnetic material into solution (magnetic wire or bar) or against the vessel or microfluidic channel, or creating an electromagnetic field using electric coils. The magnetic field retains the modified microspheres while the solution is removed.

For the next step, the microspheres having the sequestered target ions on their surface are contacted with a second solution comprising a co-ligand and an antenna ligand to form a detection solution. In one or more preferred embodiments, the co-ligand is a phosphine oxide and the antenna ligand is TTA. In preferred embodiments, the co-ligand is selected from the group consisting of CMPO, TOPO, triphenylphosphine oxide (TPPO) (FIG. 20), and combinations thereof. In one or more preferred embodiments, the ligand solution comprises TTA and CMPO, TOPO, or TPPO in a non-ionic detergent. Upon interacting with the second solution, one or more target ions on the microsphere surface get re-extracted into the detection solution, where the target ions form one or more free-floating luminescent complexes with the co-ligands and antenna ligands in the hydrophobic interior of a micelle.

The next step after magnetically separating the microspheres is to illuminate the detection solution with an appropriate wavelength to excite a luminescent response from the free-floating luminescent complexes. In a preferred embodiment, the detection solution is illuminated with 355 nm light.

To determine if any target ions were present in the initial target ion solution, the luminescent response of the detection solution to the stimulus of illumination is detected using fluorescence spectroscopy. In preferred embodiments, time-resolved laser fluorescence spectroscopy is used to detect the target luminescent ion because this calculation method measures the signal strength of the luminescent response over time, which can provide element specificity.

V. Ion-Exchange Assay

In yet another embodiment of the present invention, any of the assay methods described above for detecting the presence of luminescent target ions can be used to also detect the presence of non-luminescent target ions. The microspheres vary considerably in their capacity as ion exchangers, and this capacity can be further tuned by changing the ionic strength. In one or more embodiments, the magnetic microspheres are pre-loaded with a known concentration of a luminescent ion and mixed with a solution comprising a non-luminescent target ion to form an ion exchange solution. In this ion exchange solution, one or more non-luminescent target ions replace the luminescent ions on the magnetic microsphere surface thereby releasing one or more luminescent ions from the microsphere surface into the solution.

In one embodiment of the ion-exchange assay, carboxylated magnetic microspheres in an acidic solution also containing a non-ionic detergent are equilibrated with a known concentration of luminescent ion. In a preferred embodiment, the luminescent ion is $Eu^{3+}$. The resulting solution is mixed with a solution comprising the non-luminescent target ion. This mixture is subsequently magnetized using methods known to one of ordinary skill in the art and the supernatant is mixed with an antenna ligand and a non-ionic detergent. In one or more preferred embodiments, the antenna ligand is TTA. The luminescence of the antenna ligand is then determined in the micellar solution and compared to the luminescence of a standard antenna ligand solution. As a result, the concentration of the non-luminescent target can be determined from the following:

$$[M_{1,2}] = m_{1,2}/(K_{1,2}[L]+1), \quad (1)$$

$$[L]+[M_1]+[M_2]=[L]_0+[m_1]+[m_2], \quad (2)$$

where $K_{1,2}$ are the corresponding binding constants. Solving these equation first for the luminescent ion first, using experimental data for the luminescent ion, allows one to determine the maximum capacity $[L]_0$ for these ions and the binding constant $K_1$ and use these parameters to estimate the optimum loading $[m_1]/[L]_0$ to obtain the widest linear range of the plot of $[M_1]$ v. $[m_2]$.

EXAMPLES

One or more embodiments of the present invention are described by reference to the following examples.

For all of the examples described, the target ion used in the formation of the luminescent complexes was $Eu^{3+}$, which was introduced in and extracted from a standard solution containing $10^{-4}$ M nitric acid. These standard solutions were prepared from $Eu^{3+}$ nitrate pentahydrate using volumetric standard 1 N nitric acid. The acid concentration has been chosen to minimize $Eu^{3+}$ hydrolysis during storage.

Unless otherwise noted, the magnetic microspheres used were polystyrene microspheres from SPHEROTECH® but microspheres from any number of national and international suppliers would be appropriate. These microspheres contain metallic molecules in the core which give the microspheres magnetic properties. The microspheres are covered by a 1-μm thick protective overcoat of polystyrene on their surfaces. The surfaces of these microspheres contain sulfonate functional groups, and some microspheres are additionally functionalized with carboxyl or amino groups at the surface. The relevant properties of these polystyrene magnetic microspheres are shown in Table 1.

TABLE 1

Properties of polystyrene magnetic microspheres[a] from Spherotech.

| MM type | Diameter[b], μm | Area[c], × $10^7 nm^2$ | Surface group | $n_g^d$, per $nm^2$ | $N_g^e × 10^8$ | MMs conc, $pM^a$ |
|---------|---------|---------|---------|---------|---------|---------|
| PMS-20 | 2.5 | 1.96 | — | — | — | 4.66 |
| CMS-30 | 4.67 | 3.4 | $CO_2$ | 4.2 | 1.4 | 2.06 |
| AMS-40 | 3.28 | 6.9 | $NH_2$ | 1.7 | 1.8 | 0.7 |

[a]For a 2.5 wt % stock aqueous solution.
[b]Median diameter.
[c]Surface area per MM.
[d]Surface density of groups.
[e]Total number of groups per MM.

In all of the examples below, the luminescence was detected using time-resolved laser fluorescence (TRLF) spectroscopy. In this detection method, the sample was placed in a 10 mm×10 mm polystyrene or polymer cuvette or a 2 mL borosilicate shell vial. The sample was photoexcited using a 6 ns full-width-at-half-maximum, 1 mJ pulse of 355 nm light from a Quantel Brilliant Nd:YAG laser having a diameter of 6 mm. The emitted light was collected at 90° and passed through a narrow band (40 nm fwhm) interference filter with a transmission maximum at 620 nm. The signal was sampled using a fast photomultiplier (PMT) and terminated into 4 kΩ load at the model TDS 360 digitizing oscilloscope (Tektronix). The PMT was operated at 0.3-1.2 kV, depending on the emission yield. For weak emission signals, the PMT output was amplified by a variable gain transimpedance amplifier with 10 kΩ load at the input. For each sample, between 5 and 200 kinetic traces were sampled and averaged at 1-2 Hz. While the examples reference a specific laser and wavelengths, it is understood that any method known to one of ordinary skill in the art to excite and detect the presence of a luminescent ion may be used with the present invention.

Example 1

In a series of experiments, neutral co-ligands were covalently attached to magnetic microspheres, and a luminescent complex between the co-ligand, a target ion, and an antenna ligand formed on the surface of the microsphere. The co-ligands used in these experiments were (diphenylphosphoryl)acetic acid (FIG. 1), N,N'-bis(di-2-propyl)glycolamide (FIG. 2), di(diphenylphosphoric) imide (FIG. 3), and di(diphenylphosphoric) (2-aminoethyl) imide (FIG. 4). The co-ligands were synthesized as described in Shkrob, et al., *J. Am. Chem. Soc.* 2009, 131, 15705-15710 (Supplemental materials, pp. S3-S4), and Shkrob, et al., *Sep. Sci. & Techn.*, 45: 186-197, 2010, which are incorporated by reference herein. Each co-ligand, except for the co-ligand in FIG. 3, was covalently attached to the microspheres using the amide conjugation protocol, as described in Shkrob, *J. Am. Chem. Soc.* at S4-S6. For attaching the co-ligand of FIG. 3, a simple reaction of aminated microspheres with diphenyl phosphoryl chloride in dimethyl formamide containing pyridine as base was used instead. Shkrob, *J. Am. Chem. Soc.* at S4.

In some of these experiments, the co-ligands were not covalently bonded directly to the microspheres, but to the spacer molecules shown in FIGS. 5-12 which linked the co-ligands to the microspheres. The spacers were conjugated to the microspheres as described in Shkrob, *J. Am. Chem. Soc.* at S4-S6.

Following the attachment of the co-ligand, the magnetic microspheres were then subjected to 5-10 cycles of methanol washing followed by magnetization with periodic 1 min sonication. The last two washes were with a 0.1 wt % MEGA 10 solution, and 2.5 wt % of the modified microspheres were then suspended in 0.1 wt % MEGA 10.

In the assay analysis, 300 μL of the standard $Eu^{3+}$ in nitric acid solution were mixed with 300 μL of 1-3 mM aqueous TTA, and then 30 μL of the 2.5 wt % suspended microsphere solution were added. The solution was gently stirred for 30 sec and complexes between TTA, $Eu^{3+}$, and the synthesized co-ligand formed on the surface of the microspheres. Luminescence was detected at 30 sec intervals using TRLF.

The luminescence fully developed in 1-2 min and then gradually subsided to 50-60% of the initial yield due to slow aggregation of the microspheres. The solution was magnetized and the luminescence of the supernatant was measured to estimate the contribution from the bulk of the solvent, which was <1%. At the lowest concentration, 30 μL of 10 mM $Na_2EDTA$ was added to quench the luminescence and acquire the background signal, which was subtracted from the TRLF signal. The magnetically separated microspheres were then re-suspended in 600 μL of 0.5-1.5 mM TTA in 0.1 wt % MEGA 10 and the luminescence was again detected. In most of the experiments, 2-3 such cycles did not decrease the TRLF signal by more than 50%. The TRLF results are shown in Table 2.

TABLE 2

Relative luminescence yield in a series of trials[a].

| MMs | Spacer[d] | Ligand[d] | TRLF signal[b] | Lifetime, ms |
|---|---|---|---|---|
| AMS-40 | — | 3 | 45 | 0.200 |
| AMS-40 | — | 1 | 63 | 0.220 |
| CMS-30 | — | 4 | 91 | 0.280 |
| AMS-40* | — | 2 | 35 | 0.220 |
| CMS-30 | 7 | 3 | 25 | 0.213 |
| CMS-30 | 7 | 1 | 80 | 0.275 |
| CMS-30 | 7 | 2 | 27 | 0.250 |
| CMS-30 | 8 | 2 | 26 | 0.240 |
| AMS-40 | 9[c] | 4 | 73 | 0.240 |
| AMS-40 | 11 | 2 | 95 | 0.260 |
| CMS-30 | 12 | 1 | 43 | 0.280 |
| CMS-30 | 12 | 2 | 36 | 0.270 |

[a]The conditions of the trials: 150 nM $Eu^{3+}$ and 1.5 mM TTA in 600 μL of $5 \times 10^{-5}$ M $HNO_3$ with 0.12 wt % of the surface modified microspheres.
[b]Arbitrary units.
[c]n = 6.
[d]Numbers correspond to figure numbers.

Typical luminescence lifetimes for $Eu^{3+}$ were long enough to allow background-free detection using TRLF. All four co-ligands (FIGS. 1-4) performed equally well, although 2, 3, and 4 demonstrated greater long-term stability than 1.

The sensitivity limit of $Eu^{3+}$ was about 50 pM, and the linearity of luminescence signal persisted over 5 decades in the $Eu^{3+}$ concentration.

Example 2

Figure 20:
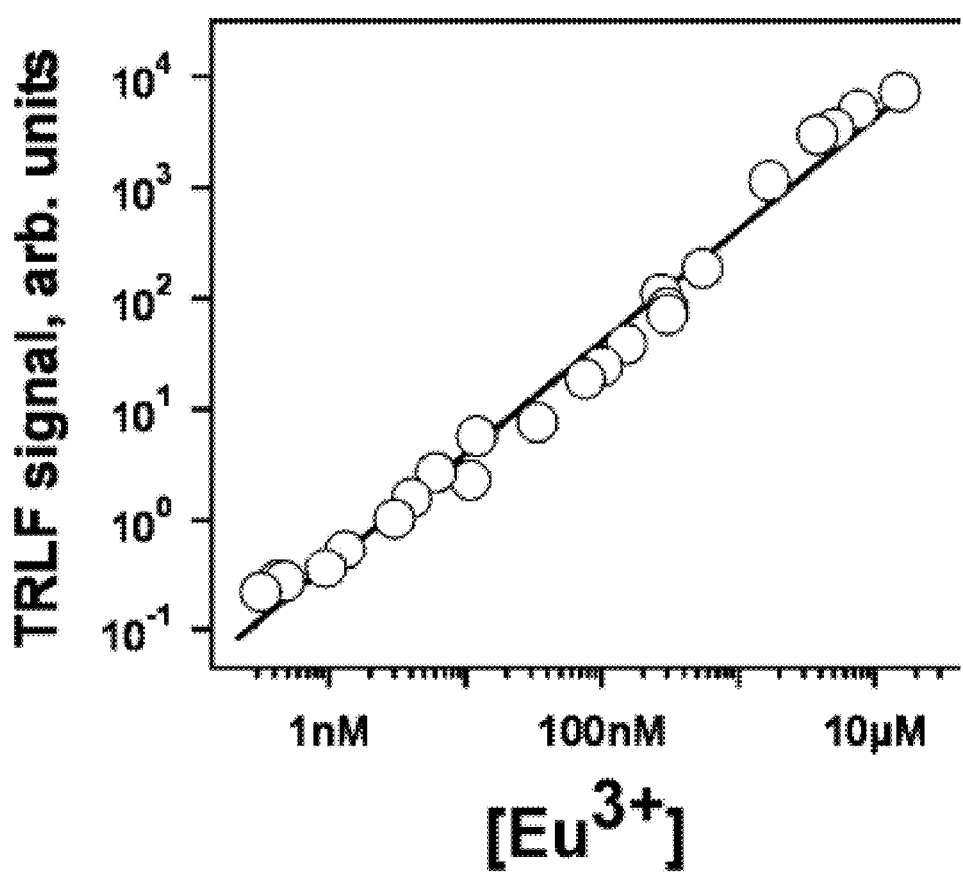
FIG. 20 represents a concentration plot showing linearity of TRLF detection for magnetic extraction of $Eu^{3+}$ by AMS-40 microspheres modified by the co-ligand in FIG. 3 in the presence of TTA.

The linearity of the detected luminescence was checked for a series of standard $Eu^{3+}$ solutions containing between 100 pM and 15 μM $Eu^{3+}$ in $10^{-4}$ M nitric acid. The results are shown in FIG. 20. Based on this linearity plot, the concentration of the target ion in a sample can be determined based on the TRLF signal.

Example 3

Polystyrene magnetic microspheres lacking amino and carboxyl groups were impregnated by a co-ligand in a NaCl solution. The high salinity in the solution allowed the co-ligand to form monolayer coverage around the microspheres, and intermolecular van der Waals forces held the co-ligand molecules in place. The repulsion between ionic atmospheres in the solution stabilized the modified magnetic microspheres.

For the first step in the modification of the microspheres, a few milligrams of the co-ligand CMPO, TOPO, or their mixture with TBP were sonicated for 3 hr at 50° C. in 300 mL of 20 wt % NaCl solution containing 0.01 wt % MEGA 10 detergent. The resulting emulsion was left to sit for 15 min and about 25 mL near the bottom of the vessel were withdrawn and filtered through a paper filter. About 1 mL of filtrate was added to PMS-20 microspheres washed by 20 wt % NaCl and suspended in 10 mL of saturated NaCl solution. This mixture was vortexed for 10 sec and then sonicated for 15 min at 50° C. The microspheres were magnetically separated and then suspended in 20 wt % NaCl solution containing 0.01 wt % MEGA 10. The cycles of magnetic separation, suspension, and sonication were repeated 5-8 times. The resulting solution of impregnated microspheres was stored in 10-20 wt % NaCl containing 0.01 wt % MEGA 10 at room temperature.

In the assay analysis, 300 µL of the standard $Eu^{3+}$ in nitric acid solution were mixed with 300 µL of 1-3 mM of aqueous TTA, and then 30 µL of the suspended microsphere solution were added. The solution was gently stirred for 30 sec and complexes between TTA, $Eu^{3+}$, and the co-ligand formed on the surface of the microspheres. The luminescence was detected every 30 sec using TRLF with the results reported in Table 3.

TABLE 3

Relative luminescence yield in a series of physisorption trials[a].

| MMs | Spacer | Ligand | TRLF signal[b] | Lifetime, MS |
|---|---|---|---|---|
| PMS-20/TOPO | — | — | 100 | 0.31 |
| PMS-20/CMPO | — | — | 71 | 0.27 |

[a]The conditions of the trials: 150 nM $Eu^{3+}$ and 1.5 mM TTA in 600 µL of $5 \times 10^{-5}$ M $HNO_3$ with 0.12 wt % of the surface modified microspheres.
[b]Arbitrary units.

The resulting luminescence lifetime was around 0.3 ms. These microspheres extracted $Eu^{3+}$ very efficiently and produced luminescence within 15 s after TTA was introduced into the analyte. This assay yielded the greatest luminescence enhancement among the surface assays analyzed.

Example 4

In this example, polystyrene magnetic microspheres were modified by covalently binding an antenna ligand to the microsphere surface. The bound antenna ligand formed a luminescent complex with the target ion and a co-ligand on the microsphere surface.

The antenna ligand TTA was bound to the magnetic microspheres by first functionalizing the TTA with a sulfate group which then bonded directly to an amino group on the microsphere surface or to a spacer molecule which linked the TTA to the microsphere surface. The functionalization is described in detail in Shkrob et al., *Sep. Sci. & Techn.*, 45: 186-197, 2010.

The luminescent complex formed when a solution of the magnetic microspheres attached to TTA molecules was added to the standard $Eu^{3+}$ solution and a third solution containing a co-ligand. The co-ligand used in this example was 0.5 mM CMPO, which was suspended in a 0.1 wt % micellar solution of Triton X-100 detergent. Like the previous examples, the luminescence was detected using TRLF spectroscopy.

This type of assay showed high sensitivity and a high tolerance for the presence of nitrate ions because the surfactant effectively isolated the complex.

Example 5

In this assay, $Eu^{3+}$ target ions were first sequestered onto the surface of modified magnetic microspheres before being introduced to the antenna ligand and forming luminescent complexes on the microsphere surfaces. In the sequestering step, 300 µL of the standard $Eu^{3+}$ solution was mixed with 30 µL of 2.5 wt % modified microspheres. The microspheres had been modified by attachment of co-ligands following the methods described above for either covalent co-ligand or physisorption assays.

After extracting the $Eu^{3+}$ ions onto the microsphere surfaces, the microspheres were magnetically separated, and then re-suspended in 600 µL of 0.5 mM TTA in 0.1 wt % MEGA 10 detergent. For physisorption assays, the TTA solution contained 10 wt % NaCl and only 0.01 wt % MEGA 10 instead of 0.1 wt % Like the previous assay methods, the luminescent complexes formed on the surface of the microspheres, and the luminescence was detected using TRLF spectroscopy.

The luminescent enhancement provided by this pre-extraction method was similar if not higher than the enhancement measured through the covalent co-ligand binding method.

Example 6

In this assay, the magnetic microspheres were modified by attachment of hydrophobic chains onto the microsphere surfaces. The hydrophobic chains allowed the microsphere to acquire a vesicle-like double layer when suspended in a hydrophilic substance. The double layer then extracted luminescent complexes onto the hydrophobic shell at the microsphere surface.

The vesicle-like double layer was formed in two ways. In the first approach, amino-conjugated magnetic microspheres were reacted with $C_{10}$-$C_{22}$ alkyl bromides or iodides in a methanol and isopropanol mixture saturated with sodium hydroxide to produce hydrophobic alkyl chains bound to the microsphere surface. The mixture was refluxed for 24 hr, and then the modified microspheres were multiply washed by ethanol with intermittent sonication for 1 min periods. Finally, the microspheres were suspended in 0.1 wt % MEGA 10 solution to prevent aggregation.

For the second approach, carboxyl-conjugated magnetic microspheres were covalently bound to a diamine and the free amino group was then attached to a carboxylated polyethylene glycol oligomer. The combination of the hydrophobic diamine chain with the hydrophilic PEG oligomer tail resulted in a "detergent-like" compound, which suspended the microspheres without the need for any detergent.

Once the magnetic microspheres were modified by either approach, they were mixed with the standard $Eu^{3+}$ solution and an aqueous solution containing 0.75 mM antenna ligand TTA and 0.25 mM co-ligand TBP. These ligands were extracted into the hydrophobic layer of the microspheres, where they formed luminescent complexes with the target ion $Eu^{3+}$. The luminescence was detected using TRLF.

Extracting the luminescent complexes onto the hydrophobic shell increased luminescence by 25 times. The detected luminescence lifetimes were 0.25-0.35 ms.

Example 7

In this assay, the luminescent complex is formed in the micellar solution independent of the magnetic microspheres, although the microspheres are still used for the initial sequestration of target ions from the standard solution. In order to extract $Eu^{3+}$ target ions, the magnetic microspheres had been modified by covalent attachment to aminocarboxylic acids. Preferred embodiments used cellulose (e.g., SEPHAROSE®) microspheres conjugated with EDTA and silica microspheres conjugated with IDA. The properties of these microspheres are found in Table 4. However, it is believed that any microsphere modified with an aminocarboxylic acid will be capable of extracting a target ion and, thus, will be compatible with the method of the present example.

TABLE 4

Properties of MMs used for solution-based assay extractions.

| MM | Name | Manufacturer | Diameter | Concent. | Binding Capacity |
|---|---|---|---|---|---|
| EDTA/ Cellulose | MagaCell-EDTA | Cortex Biochem | 10 μm | 5 wt % | 50 μmol $Ni^{2+}$/g MM |
| IDA/Silica | BcMag-IDA | BioClone | 1 μm | 2 wt % | 55 μmol $Ni^{2+}$/g MM |

For the initial sequestration, a solution of modified magnetic microspheres suspended in 0.1 wt % Triton X-100 detergent was stirred with 1 mL of standard $Eu^{3+}$ solution for 1 min. After the sequestration step, the microspheres were magnetically separated. Next, the microspheres were contacted with 500 μL of 0.1 wt % Triton X-100 solution containing 0.5 mM of antenna ligand TTA and 0.5 mM of a neutral co-ligand, such as CMPO, TOPO or TPPO. The resulting solution was stirred for 1 min as the ligands re-extracted $Eu^{3+}$ target ions from the microspheres and formed luminescent complexes in the micellar solution. The microspheres were then magnetically separated, and the luminescence in the solution was detected using TRLF.

This example proved to be the most sensitive assay, with a detection limit of 0.1 pM. Typical luminescence lifetimes were 0.65-0.72 ms, and the detection signal was linear with the concentration of $Eu^{3+}$ from 0.1 pM-1 μM.

Example 8

In this example, luminescent assays can be used to detect the presence of non-luminescent ions. In this procedure, luminescent $Eu^{3+}$ ions were pre-loaded onto microspheres by equilibrating 4.3 μM $Eu^{3+}$ with 250 μL of a 0.07 wt % suspension of CMS-30 carboxylated magnetic microspheres in $10^{-4}$ M nitric acid also containing 0.1 wt. % Triton X-100. It was determined that for 0.07 wt. % CMS-30 in $10^{-4}$ $HNO_3$ containing 0.1 wt. % Triton X-100, $[L]_0 \approx 4.6$ μM and $K_1[L]_0 \approx 60$. The resulting solution was mixed with 250 μL of gadolinium ions ($Gd^{3+}$) in $10^{-4}$ M nitric acid, stirred for 1 min, and then magnetized. At this point, the $Gd^{3+}$ ions replaced the $Eu^{3+}$ ions on the microspheres, and the excised $Eu^{3+}$ ions became free-floating in the supernatant solution.

Once the dislodged luminescent ions were in the supernatant, their presence was detected by performing any of the assay methods described above in Examples 1-7. For example, to perform a solution-based assay, 50 μL of supernatant were mixed with 1.5 mL of 0.5 mM TTA and 0.5 mM CMPO in 0.1 wt % Triton X-100, and the luminescence was detected using TRLF.

Figure 21:
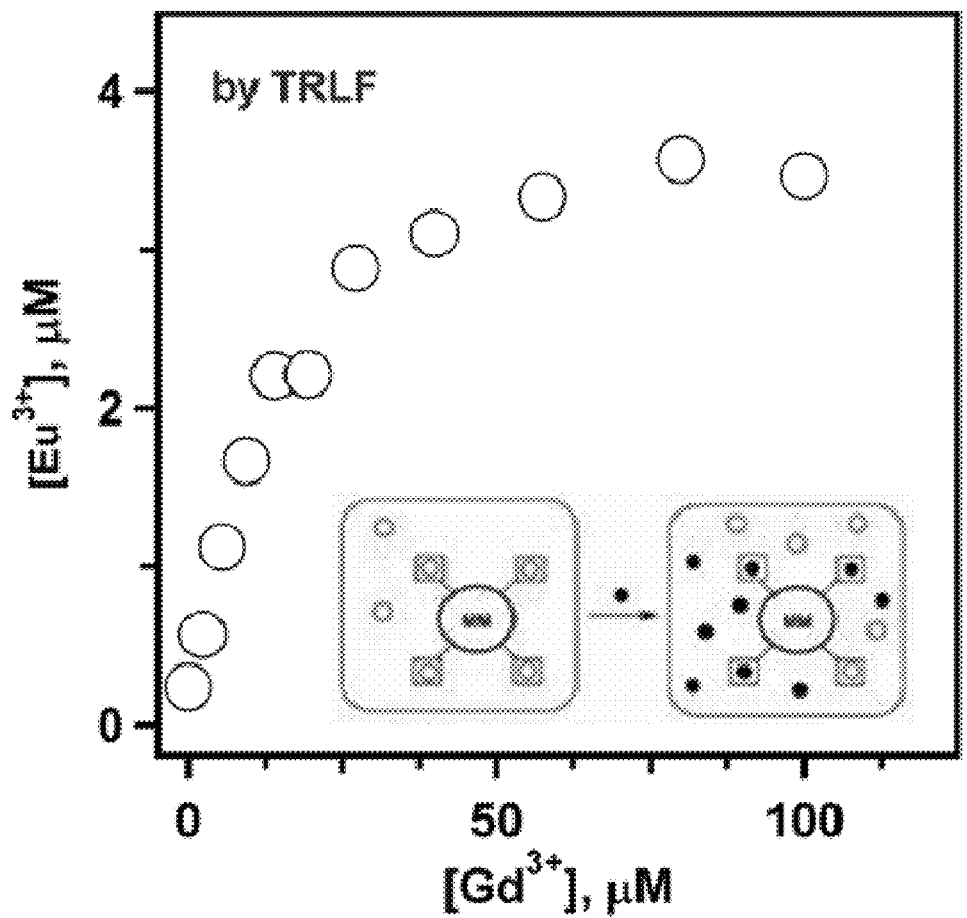
FIG. 21 represents a plot showing the $Eu^{3+}/Gd^{3+}$ ion exchange assay for PMS-20 microspheres loaded with $Eu^{3+}$, where the $Eu^{3+}$ concentration in the supernatant was determined using a solution-based assay.
Figure 22:
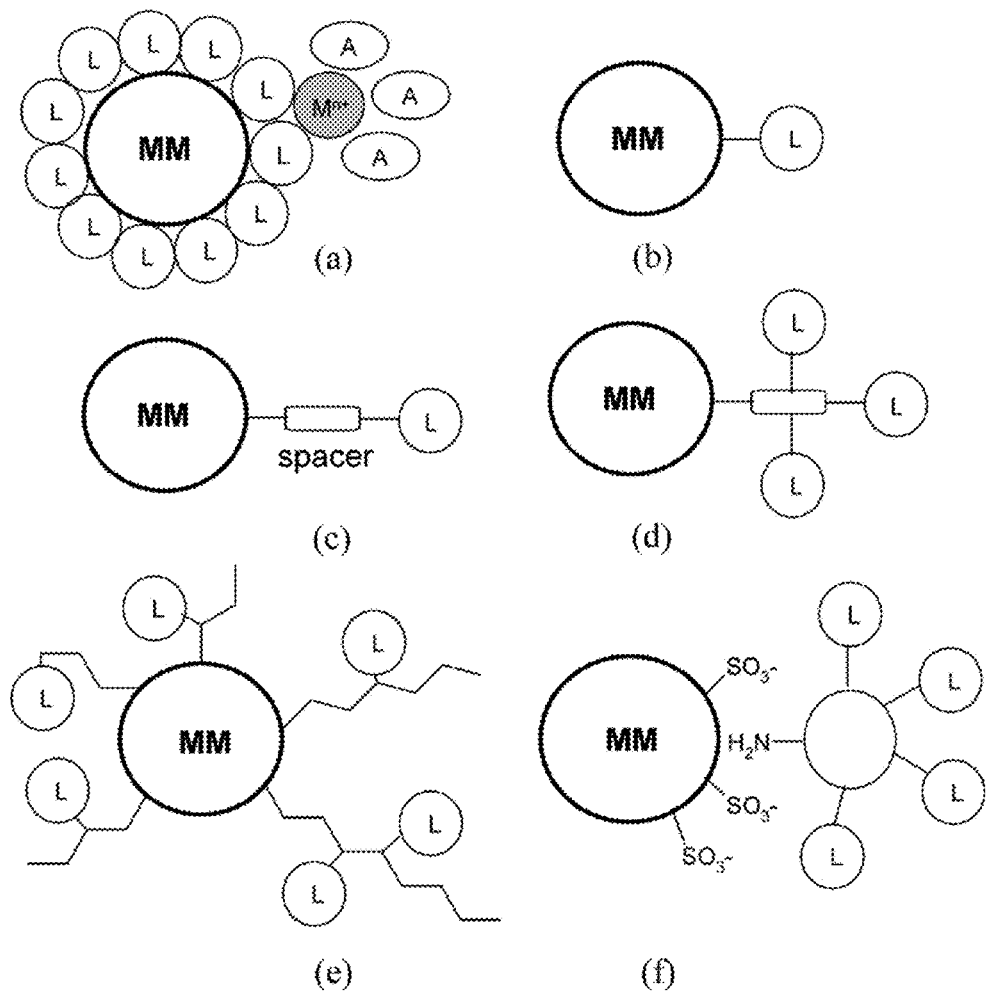
FIGS. 22A-F are schematic representations of one or more embodiments of the present invention wherein a co-ligand is modified through attachment to a modified microsphere.

As the concentration of non-luminescent $Gd^{3+}$ ions increases, so too does the concentration of excised luminescent $Eu^{3+}$ ions in the supernatant. Thus, the concentration of the non-luminescent ion can be estimated by comparing the luminescence derived by the excised $Eu^{3+}$ ions to that of a standard $Eu^{3+}$ solution. The results are shown in FIG. 21. As indicated in FIG. 22, the luminescent signal was linear with the concentration of $Gd^{3+}$ up to 30 μM. This assay can be adapted to detect lower concentrations of $Gd^{3+}$ ions by decreasing the concentration of the CMS-30 microspheres and $Eu^{3+}$ ion accordingly. As described above, it is possible to detect non-luminescent ions using a combination of the mixed-ligand surface assays described in Examples 1-7 and the ion exchange method described in this Example.

It is to be understood that the above-described arrangements are only illustrative of the application of the principles of the present invention and they are not intended to be exhaustive or limit the invention to the precise forms disclosed. Numerous modifications and alternative arrangements may be devised by those skilled in the art in light of the above teachings without departing from the spirit and scope of the present invention. It is intended that the scope of the invention be defined by the claims appended hereto.

In addition, the previously described versions of the present invention have many advantages, including but not limited to those described above. However, the invention does not require that all advantages and aspects be incorporated into every embodiment of the present invention.

All publications and patent documents cited in this application are incorporated by reference in their entirety for all purposes to the same extent as if each individual publication or patent document were so individually denoted.

We claim:

1. A method of detecting a luminescent target ion in a sample comprising:
   a. Mixing a solution comprising modified magnetic microspheres with a solution comprising a target ion which is a luminescent ion selected from the group consisting of Eu, Tb, Am, U and combinations thereof and a solution comprising a second ligand to form a detection solution, wherein the magnetic microspheres have a non-reactive barrier selected from the group consisting of gold, carbon, oxide, polymer and combinations thereof are modified through attachment of a first ligand capable of forming a complex with the target ion and the second ligand wherein the first ligand is a co-ligand and the second ligand is an antenna ligand, and wherein the co-ligand is a compound selected from the group consisting of phosphine oxides, organophosphates, diglycolamides, bidentate imides and combinations thereof, and wherein one or more first ligand/target ion/second ligand complexes are formed on the surface of the magnetic microsphere in the detection solution; and
   b. performing Time-resolved laser fluorescence (TRLF) spectroscopy is used to illuminate the detection solution and detect the luminescent response from the ligand complex.

2. The method of claim 1, wherein the antenna ligand is selected from the group consisting of diketones, beta-diketones substituted with at least one aromatic group, acetylacetone derivatives, phenanthroline derivatives and combinations thereof.

3. The method of claim 1, wherein the antenna ligand comprises TTA and the co-ligand comprises a phosphine oxide.

4. The method of claim 3, wherein the solution comprising the co-ligand comprises a non-ionic detergent.

5. The method of claim 1, wherein the antenna ligand comprises an acetylacetone derivative.

6. The method of claim 5, wherein the antenna ligand is 2-thenoyltrifluoroacetone (TTA).

7. The method of claim 6, wherein the solution comprising magnetic microspheres comprises a non-ionic detergent.

8. The method of claim 7, wherein the solution comprising magnetic microspheres further comprises a saline solution.

9. A method of detecting a luminescent target in a sample comprising:

a. Mixing a solution comprising modified magnetic microspheres with a solution comprising a target ion which is a luminescent ion selected from the group consisting of Eu, Tb, Am, U and combinations thereof and a solution comprising a second ligand to form a detection solution, wherein the magnetic microspheres have a non-reactive barrier selected from the group consisting of gold, carbon, oxide, polymer and combinations thereof are modified through attachment of a first ligand capable of forming a complex with the target ion and the second ligand wherein the first ligand is a co-ligand and the second ligand is an antenna ligand and wherein the co-ligand is selected from the group consisting of CMPO, TOPO, TPO, TBP, (diphenylphosphoryl)acetic acid, N,N'-bis (di-2-propyl)glycolamide, di(diphenylphosphoric) imide, di(diphenylphosphoric)(2-aminoethyl)imide and combinations thereof, and wherein one or more first ligand/target ion/second ligand complexes are for aged on the surface of the magnetic microsphere in the detection solution; and b. performing Time-resolved laser fluorescence(TRLF) spectroscopy is used to illuminate the detection solution and detect luminescent response from the ligand complex.

10. A method of detecting a luminescent target ion in a sample comprising:

a. Mixing a solution comprising modified magnetic microspheres and a non-ionic detergent with a solution comprising a target ion wherein the target ion is a luminescent ion selected from the group consisting of Eu, Tb, Am, U and combinations thereof and an aqueous solution comprising both an antenna ligand and a co-ligand wherein the antenna ligand is selected from the group consisting of diketones, beta-diketones substituted with at least one aromatic group, acetylacetone derivatives, phenanthroline derivatives and combinations thereof and the co-ligand is a compound selected from the group consisting of phosphine oxides, organophosphates, diglycolamides, bidentate imides and combinations thereof thereby forming a detection solution, wherein one or more co-ligand/target ion/antenna ligand complexes are formed in the detection solution, and wherein the microsphere comprises a non-reactive barrier selected from the group consisting of gold, carbon, oxide, polymer and combinations thereof and is modified through attachment of a hydrophobic chain capable of extracting one or more ligand complexes from the detection solution onto the microsphere surface;

b. Illuminating the complex with an appropriate wavelength to excite a luminescent response from the complex; and detecting the luminescent response.

11. The method of claim 10, wherein the hydrophobic chain is an alkyl group comprising between 10 and 22 carbon atoms.

12. The method of claim 10, wherein the hydrophobic chain is a diamine compound attached to a polyether compound.

13. A method of detecting a luminescent target ion in a sample comprising:

a. Mixing modified magnetic microspheres with a solution comprising a target ion, wherein the microspheres are modified with a functional group, and further wherein the functional group binds the target ion, forming a non-luminescent complex on the microsphere surface;

b. Magnetically separating the microspheres from the solution;

c. Contacting the microspheres with a solution comprising a co-ligand and an antenna ligand to form a detection solution, wherein the co-ligand and antenna ligand extract the target ion from the non-luminescent complex on the microsphere surface, and wherein one or more luminescent ligand complexes comprising the co-ligand, the target ion, and the antenna ligand form in the detection solution;

d. Illuminating the detection solution with an appropriate wavelength to excite a luminescent response from the luminescent ligand complex; and, e. Detecting the luminescent response.

14. The method of claim 13, wherein the functional group of the modified microsphere is selected from the group consisting of ethylenediaminetetraacetic acid (EDTA), iminodiacetic acid (IDA) and combinations thereof, wherein the solution comprising the co-ligand and antenna ligand comprises a detergent, wherein the target ion is a luminescent ion selected from the group consisting of Eu, Tb, Am, U and combinations thereof, and, further wherein the co-ligand is a compound selected from the group consisting of phosphine oxides, organophosphates, diglycolamides, bidentate imides and combinations thereof and the antenna ligand is selected from the group consisting of diketones, beta-diketones substituted with at least one aromatic group, acetylacetone derivatives, phenanthroline derivatives and combinations thereof.

15. A method of detecting a luminescent target ion in a sample comprising:

a. Mixing a solution comprising modified magnetic microspheres with a solution comprising the target ion, wherein the magnetic microspheres are modified through attachment of a co-ligand, and further wherein the co-ligand on the microsphere surface extracts one or more target ions from the target ion solution forming one or more non-luminescent complexes on the magnetic microsphere surface;

b. Magnetically separating the magnetic microspheres;

c. Contacting the magnetic microspheres with a solution comprising an antenna ligand to form a detection solution, wherein one or more luminescent ligand complexes comprising the antenna ligand, the target ion, and the co-ligand are formed on the magnetic microsphere surface within the detection solution;

d. Illuminating the detection solution with an appropriate wavelength to excite a luminescent response from the luminescent ligand complex; and, e. Detecting the luminescent response.

16. The method of claim 15, wherein the target ion is a luminescent ion selected from the group consisting of Eu, Tb, Am, U and combinations thereof, wherein the solution comprising the modified magnetic microspheres comprises a non-ionic detergent, wherein the co-ligand is a compound selected from the group consisting of phosphine oxides, organophosphates, diglycolamides, bidentate imides and combinations thereof, and wherein the antenna ligand is selected from the group consisting of diketones, beta-diketones substituted with at least one aromatic group, acetylacetone derivatives, phenanthroline derivatives and combinations thereof.

* * * * *